United States Patent
Abe et al.

(10) Patent No.: US 9,371,268 B2
(45) Date of Patent: Jun. 21, 2016

(54) METHOD FOR PRODUCING ASYMMETRIC CHAIN CARBONATE

(75) Inventors: Koji Abe, Yamaguchi (JP); Akikazu Ito, Yamaguchi (JP)

(73) Assignee: UBE INDUSTRIES, LTD., Ube-shi, Yamaguchi (JP)

(*) Notice: Subject to any disclaimer, the term of this patent is extended or adjusted under 35 U.S.C. 154(b) by 0 days.

(21) Appl. No.: 13/061,329

(22) PCT Filed: Aug. 31, 2009

(86) PCT No.: PCT/JP2009/065201
§ 371 (c)(1),
(2), (4) Date: Feb. 28, 2011

(87) PCT Pub. No.: WO2010/024438
PCT Pub. Date: Mar. 4, 2010

(65) Prior Publication Data
US 2011/0152559 A1    Jun. 23, 2011

(30) Foreign Application Priority Data
Sep. 1, 2008  (JP) .................. 2008-223241

(51) Int. Cl.
*C07C 69/96*    (2006.01)
*C07C 68/00*    (2006.01)

(52) U.S. Cl.
CPC .................................. *C07C 68/00* (2013.01)

(58) Field of Classification Search
None
See application file for complete search history.

(56) References Cited

U.S. PATENT DOCUMENTS

| 5,162,563 | A | | 11/1992 | Nishihira et al. | |
|---|---|---|---|---|---|
| 5,631,396 | A | * | 5/1997 | Nishihira et al. | 558/277 |
| 5,688,984 | A | | 11/1997 | Ohdan et al. | |
| 5,869,729 | A | * | 2/1999 | Nishihira et al. | 558/277 |

FOREIGN PATENT DOCUMENTS

| CN | 1562957 | | 1/2005 | |
|---|---|---|---|---|
| JP | 08-253443 | * | 10/1996 | C07C 69/96 |

OTHER PUBLICATIONS

Machine translation of JP 08-253443. Obtained from <http://dossier.ipdl.inpit.go.jp/text_trans.html>. Accessed on Nov. 22, 2012.*
Chinese Office Action (Application No. 2013011800764130) dated Jan. 23, 2013.
Extended European Search Report mailed Jul. 24, 2015 issued in an European Patent Application No. 09810082.

* cited by examiner

*Primary Examiner* — Alicia L Otton
(74) *Attorney, Agent, or Firm* — Nixon Peabody LLP; Jeffrey L. Costellia

(57) ABSTRACT

An asymmetric chain carbonate can be produced in a single-step reaction comprising a step of reacting methyl nitrite, carbon monoxide, and 0.05-1.5 moles of an aliphatic alcohol having 2-6 carbon atoms or an alicyclic alcohol having 5-6 carbon atoms per one mole of methyl nitrile in a gaseous phase in the presence of a solid catalyst comprising a platinum group metal or a compound thereof placed on a support.

4 Claims, No Drawings

METHOD FOR PRODUCING ASYMMETRIC CHAIN CARBONATE

FIELD OF THE INVENTION

The present invention relates to a method for producing an asymmetric chain carbonate.

BACKGROUND OF THE INVENTION

JP-A-6-72966 describes a method for producing a symmetric chain carbonic acid diester such as dimethyl carbonate which comprises a step of catalytically reacting a nitrous acid ester with carbon monoxide in a gas phase.

JP-A-6-92910 describes a method for producing a symmetric chain carbonic acid diester such as dimethyl carbonate which comprises a step of catalytically reacting an nitrous acid ester with carbon monoxide in a presence of water and a solid catalyst comprising a platinum group metal ion placed on a zeolite support. It is described that the symmetric chain carbonic acid diester such as dimethyl carbonate can be produced in a high yield because the activity of the solid catalyst is kept at a high level for a long period.

As for a method for producing an asymmetric chain carbonate, JP-A-10-237026 describes a method comprising disproportionation reaction between two kinds of beforehand prepared symmetric chain carbonate in a liquid phase using a catalyst comprising titanium oxide as an active catalyst component, to produce the desired asymmetric chain carbonate.

The method described in JP-A-10-237026 is, however, not advantageous as an industrially applicable method, because the method requires the two producing steps for preparing two kinds of symmetric chain carbonates and subsequently subjecting these carbonates to the disproportionation reaction. Further, there is a problem that the yield of the asymmetric chain carbonate obtained from the equilibrium mixture produced by the disproportionation reaction is low (at most 43.5%, in terms of the yield based on the amount of the charged starting materials).

SUMMARY OF THE INVENTION

The present invention has an object to provide a method for producing an asymmetric chain carbonate by one step reaction. Specifically, the invention has an object to provide a method for producing an asymmetric chain carbonate by one step reaction with a high reaction rate (space time yield) and a high selectivity.

The present inventors have found that an asymmetric chain (or linear) carbonate can be produced by one step reaction (one path reaction) with a high reaction rate (space time yield) and a high selectivity in which the step of reacting methyl nitrite and carbon monoxide in a gaseous phase in the presence of a solid catalyst comprising a platinum group metal or a compound thereof placed on a support is performed in the presence 0.05-1.5 moles of an alcohol per one mole of methyl nitrite, the alcohol being an aliphatic alcohol having 2-6 carbon atoms or an alicyclic alcohol having 5-6 carbon atoms. The present invention is based on the above-mentioned finding.

Accordingly, the present invention resides in a method for producing an asymmetric chain carbonate comprising a step of reacting methyl nitrite, carbon monoxide and 0.05-1.5 moles of a lower alcohol per one mole of methyl nitrite, the lower alcohol being selected from the group consisting of an aliphatic alcohol having 2-6 carbon atoms and an alicyclic alcohol having 5-6 carbon atoms, in a gaseous phase in the presence of a solid catalyst comprising a platinum group metal or a compound thereof placed on a support.

Effects of the Invention

According to the present invention, an asymmetric chain carbonate can be produced in a one step reaction with a high reaction rate (space time yield) and a high selectivity.

PREFERRED EMBODIMENTS OF THE INVENTION

The method for producing an asymmetric chain carbonate according to the invention is characterized in that the method is performed by reacting methyl nitrite, carbon monoxide and 0.05-1.5 moles of a lower alcohol per one mole of methyl nitrite, the lower alcohol being selected from the group consisting of an aliphatic alcohol having 2-6 carbon atoms and an alicyclic alcohol having 5-6 carbon atoms, in a gaseous phase in the presence of a solid catalyst comprising a platinum group metal or a compound thereof placed on a support.

Preferred embodiments of the invention are described below.

(1) The lower alcohol is an aliphatic alcohol having 2-6 carbon atoms.

(2) The lower alcohol is an aliphatic alcohol having 2-6 carbon atoms is an alcohol selected from the group consisting of ethanol, 1-propanol, 2-propanol, 1-butanol, 2-methyl-1-propanol, 2-butanol, and 2-methyl-2-propanol.

(3) The lower alcohol is an aliphatic alcohol having 2-6 carbon atoms is ethanol or 2-propanol and the produced asymmetric carbonate is methyl ethyl carbonate or methyl isopropyl carbonate, respectively.

(4) The lower alcohol is used in an amount of 0.1 to 1.2 moles per one mole of methyl nitrite.

(5) The lower alcohol is used in an amount of 0.2 to 1.0 mole per one mole of methyl nitrite.

(6) The catalyst comprising a platinum group metal or a compound thereof comprises palladium or a compound thereof selected from the group consisting of a palladium halide, an inorganic acid salt of palladium and an organic acid salt of palladium, the palladium or the compound being placed on the support in an amount of 0.1 to 10 wt. %.

(7) The catalyst comprising a platinum group metal or a compound thereof contains a copper compound.

(8) The support of the solid catalyst is a porous support.

(9) The porous support comprises a material selected from the group consisting of carbon, alumina, silica, silica alumina, zeolite, and lithium aluminate having a spinel structure.

(10) The reaction is performed in the presence of methanol in an amount of 0.005 to 1 mole per one mole of the lower alcohol.

(11) The reaction is performed under supply of hydrogen chloride in an amount of 0.01 to 1 mole/hr. per one mole of the platinum group metal in the catalyst.

The method of the invention for producing an asymmetric chain carbonate is further described with reference to the starting compounds, catalyst, auxiliary additives, and reaction conditions.

Examples of the aliphatic alcohol having 2-6 carbon atoms include ethanol, 1-propanol, 2-propanol (isopropyl alcohol), 1-butanol, 2-methyl-1-propanol, 2-butanol and 2-methyl-2-propanol. Example of the alicyclic alcohol having 5-6 carbon atoms include cyclopentanol and cyclohexanol. Ethanol and 2-propanol are most preferred, because the gaseous reaction phase is kept even after the desired asymmetric chain carbonate (methyl ethyl carbonate or methyl isopropyl carbonate) is produced and further the catalyst life is long.

The alcohol is preferably employed in an amount of 0.05 to 1.5 moles, more preferably 0.1 to 1.2 moles, most preferably 0.2 to 1.0 mole, per one mole of methyl nitrite, so that the desired product can be obtained with a high reaction rate (space time yield) and a high selectivity.

Examples of the asymmetric chain carbonates produced by the invention utilizing the lower alcohol include methyl ethyl carbonate, methyl propyl carbonate, methyl isopropyl carbonate, methyl butyl carbonate, methyl secbutyl carbonate, methyl tert-butyl carbonate, methyl cyclopentyl carbonate, and methyl cyclohexyl carbonate.

The catalyst employed in the invention is a platinum group metal such as palladium, platinum, iridium, ruthenium or rhodium, or a compound of one of the platinum group metal. Examples of the compounds of the platinum group metals include halides such as chloride, bromide, iodide and fluoride, inorganic acid salts such as nitrate and sulfate, organic acid salts such as acetate and benzoate, and complex compounds such as halide-containing complex compounds and amine complex compound. In more detail, there can be mentioned palladium compounds such as halides (e.g., palladium chloride and palladium bromide), inorganic acid salts (e.g., palladium nitrate and palladium sulfate), organic acid salts (e.g., palladium acetate and palladium benzoate), halide-containing complex compounds (e.g., lithium tetrachloropalladiumate and sodium tetrachloropalladiumate), and amine complex compounds (e.g., tetramminepalladium chloride and tetramminepalladium nitrate).

Preferred are halides of palladium, platinum, ruthenium and rhodium. Specifically preferred is a chloride. Palladium chloride is most preferred for its high reaction activity. The catalyst can be placed on a support in an amount of, preferably, 0.1 to 10 wt. %, most preferably 0.5 to 3 wt. %.

The platinum group metal and its compounds can be used in combination with various auxiliary components. For example, halides (e.g., chloride, bromide, iodide, fluoride), inorganic acid salts (e.g., nitrate, sulfate, phosphate), and organic acid salts (e.g., acetate) of metals such as iron, copper, bismuth, cobalt, nickel and tin can be used. In more detail, there can be mentioned ferrous chloride, ferric chloride, cupric chloride, bismuth chloride, cobalt(II) chloride, nickel chloride, tin(II) chloride, ferric bromide, nickel bromide, ferrous acetate, cobalt(II) acetate, tin(II) acetate, and nickel nitrate. A preferred auxiliary component is a halide of copper. Particularly preferred is cupric chloride because it can accelerate the catalytic activity. The auxiliary component can be used in an amount of 0.03 to 30 moles, particularly, 0.1 to 10 moles, per one mole of the platinum group metal of the platinum group metal compound.

It is preferred that the catalyst is placed on a porous support, particularly a porous support having a specific surface area in the range of 0.1 to 5,000 $m^2/g$, for the reason that the platinum group metal catalyst can be finely dispersed on the support and efficiently function as the catalyst.

Examples of the porous support include carbon (including active carbon) having a specific surface area of 500-3,000 $m^2/g$, preferably 600-2,000 $m^2/g$, alumina having a specific surface area of 30-350 $m^2/g$, preferably 50-300 $m^2/g$, silica having a specific surface area of 80-750 $m^2/g$, preferably 100-700 $m^2/g$, silica-alumina having a specific surface area of 65-650 $m^2/g$, preferably 100-550 $m^2/g$, zeolite having a specific surface area of 150-800 $m^2/g$, lithium aluminate of spinel structure ($Li_xAl_5O_{(15+x)/2}$, wherein x is 0.5 to 1.5) having a specific surface area of 20-500 $m^2/g$, preferably 30-300 $m^2/g$, polymer having a specific surface area of 150-250 $m^2/g$, preferably 160-240 $m^2/g$, diatomaceous earth having a specific surface area of 5-170 $m^2/g$, preferably 10-150 $m^2/g$, magnesium salt, barium salt and calcium salt.

Preferred porous supports are carbon (including active carbon), alumina, silica, silica-alumina, zeolite, and lithium aluminate of spinel structure. More preferred supports are carbon (including active carbon), alumina, zeolite, and lithium aluminate of spinel structure. The most preferred support is the lithium aluminate.

The porous lithium aluminate support employable in the method of the invention can be produced by placing alumina particles having a specific surface area of 30 $m^2/g$ or more in an aqueous lithium salt solution, drying the thus treated alumina particles, and calcinating the dried alumina particles at a temperature of 500° C. or higher. The porous lithium aluminate support can be also produced by mixing alumina sol and an aqueous lithium salt solution, drying the mixture, and calcinating the dried mixture at a temperature of 500° C. or higher.

In the method of the invention, the gaseous starting materials comprising methyl nitrite and carbon monoxide contains carbon monoxide in an amount of 0.1 to 10 moles, preferably 0.2 to 2 moles, so as to enhance the reaction rate (space time yield) and the selectivity.

In the invention, methyl nitrite and carbon monoxide are preferably introduced into a reaction vessel after they are independently or in the form of a mixture diluted with an inert gas. There is no specific limitation with respect to the amount of the inert gas. However, it is preferred that a diluted methyl nitrite gas contains 5 to 20 vol. %, in view of safety and reaction efficiency. The carbon monoxide concentration in the starting gaseous mixture can be adjusted up to 80 vol. % if the carbon monoxide gas is employed as the inert gas. However, the carbon monoxide concentration exceeding 20 vol. % is meaningless, because the gaseous starting material is generally used in industry under circulation with a partial purging of the gaseous mixture and the conversion ratio of carbon monoxide in one path is approximately 20% to 30%. However, if the carbon monoxide concentration is 5 vol. % or less, the productivity decreases. Therefore, it is preferred that the carbon monoxide concentration in the starting gaseous material is adjusted in the range of 5 to 20 vol. %.

There are no limitations with respect to the procedures for adding the lower alcohol to the gaseous mixture comprising methyl nitrite and carbon monoxide. The procedures can be performed by supplying a beforehand vaporized lower alcohol into the reaction vessel or by supplying liquid lower alcohol into the reaction vessel. The beforehand vaporized lower alcohol can be supplied singly or in a mixture prepared by dilution with an active gas such as nitrogen gas.

The gaseous catalytic reaction of carbon monoxide, methyl nitrite and a lower alcohol is performed under the below-mentioned mild reaction conditions after the gaseous starting gas is supplied into a reaction vessel charged with the aforementioned catalyst:

Reaction temperature: generally 0 to 200° C., preferably 50 to 150° C.,

Reaction pressure: atmospheric pressure,

Space velocity: 500 to 20,000 $hr^{-1}$, preferably 1,000 to 10,000 $hr^{-1}$, more preferably 2,000 to 5,000 $hr^{-1}$.

However, the reaction can be performed under pressure, for instance, under such conditions as a reaction temperature of 50 to 150° C. and a pressure of 1 to 20 $kg/cm^2G$. If methyl nitrite is supplied after regeneration from nitrogen monoxide, the gaseous catalytic reaction between carbon monoxide and methyl nitrite is preferably performed under pressure such as a pressure of 1 to 5 $kg/cm^2G$. The gaseous catalytic reaction can be performed in any processes such as a batch process and a continuous process using a fixed bed, a moving bed or a fluid bed. However, the continuous process using a fixed bed is preferably performed in commercially available plants. The reaction vessel can be of any types, so far as the gaseous catalytic reaction can be performed in the reaction vessel.

The gaseous starting material comprising methyl nitrite and carbon monoxide for the use in the method of the invention preferably contains a small amount of methanol. If the amount of methanol is too small, the reaction rate (space time yield) decreases. However, if the amount of methanol is too large, dimethyl carbonate is predominantly produced. Therefore, the methanol is incorporated in an amount of 0.005 to 1 mole, preferably 0.01 to 0.8 mole, most preferably 0.05 to 0.5 mole, per one mole of the aliphatic alcohol having 2-6 carbon atoms (or the alicyclic alcohol having 5-6 carbon atoms) which is employed for the production of an asymmetric chain carbonate.

Accordingly, the total amount of methanol and the aliphatic alcohol having 2-6 carbon atoms (or the alicyclic alcohol having 5-6 carbon atoms) for the production of an asymmetric chain carbonate according to the method of the invention is in the range of 0.05 to 3 moles, preferably 0.1 to 2.2 moles, most preferably 0.33 to 1.5 moles. If the total amount of alcohols is too small, the reaction activity decreases so that the reaction rate (space time yield) and selectivity lowers. If the total amount is too large, the reaction mixture may become liquid and may be placed under reductive condition due to excessive alcohols, whereby the catalyst life shortens.

It is preferred that hydrogen chloride is present in the mixture of methyl nitrite and carbon monoxide for the production of an asymmetric chain carbonate, so as to keep the activity of catalyst from lowering. Hydrogen chloride preferably is anhydrous hydrogen chloride. Hydrogen chloride can be incorporated into the reaction mixture by any methods. However, the below-described continuous incorporation of a small amount of hydrogen chloride is preferably employed. Hydrogen chloride is incorporated in an amount of 0.01 to 1 mole, preferably 0.02 to 0.2 mole, in one hour, per one mole of the platinum group metal in the catalyst. If the amount of hydrogen chloride is too large, the reaction may be disturbed due to adsorption of hydrogen chloride by the catalyst. The incorporation of hydrogen chloride can be carried out, for instance, hydrogen chloride is continuously added to the gaseous starting material in the reaction vessel in an amount of 5 to 500 vol.ppm, preferably in an amount of 10 to 100 vol.ppm, when the reaction is performed in the reaction vessel having a fixed bed at a gas space velocity (GHSV) of 3,000 hr$^{-1}$.

Otherwise, a gaseous chlorine-containing compound such as gaseous chloroformate can be used in place of hydrogen chloride. The incorporation of a gaseous chlorine-containing compound such as gaseous chloroformate also can be effective to keep the catalyst activity from lowering. Examples of the chloroformate include esters of chloroformic acid and a monovalent lower aliphatic alcohol having 1-4 carbon atoms such as methyl chloroformate, ethyl chloroformate, n-(or iso) propyl chloroformate, n-(or iso or sec.)butyl chloroformate. The chloroformate also is preferably incorporated continuously. In the continuous incorporation of chloroformate, there is no specific limitation with respect to the amount of chloroformate. However, chloroformate is generally supplied continuously into the gaseous starting material in an amount of 1 vol. % or less, preferably 1,000 vol.ppm or less, from the economic view point in consideration of industrially employable methods. In the actual procedure, a nitrogen gas is passed in contact with warmed chloroformate so that the nitrogen gas can be accompanied by vaporized chloroformate. Otherwise, chloroformate is vaporized in a vaporizer independently attached to the reaction vessel and the vaporized chloroformate is introduced with nitrogen gas.

The desired asymmetric chain carbonate can be produced by performing a gaseous catalytic reaction of methyl nitrite and carbon monoxide in the presence of an aliphatic alcohol having 2-6 carbon atoms (or an alicyclic alcohol having 5-6 carbon atoms). The desired product can be recovered from the reaction vessel in the form of a gaseous mixture containing the gaseous starting material. The gaseous mixture is cooled to give a condensate, which is then subjected to a conventional isolation/purification procedure such as distillation.

EXAMPLES

The invention is further described by the below-described working examples and reference examples.

In the examples, the space time yield (STY, in terms of Y (g/L·hr)) of the asymmetric chain carbonate was calculated according to the following formula:

$Y(g/L \cdot hr) = a(g)/(V(L) \times \theta(hr))$

In the formula, "θ(hr)" represents a period of time for the catalytic reaction of the gaseous mixture on the catalyst, "a (g)" represents an amount of produced asymmetric chain carbonate by the catalytic reaction, and "V (L)" represents the amount of the catalyst charged in the reaction tube.

The selectivity (X) of production of the asymmetric chain carbonate in the examples was calculated according to the following formula:

$X(\%) = (a/(a+b+c)) \times 100$

In the formula, "a", "b", and "c" represent molar amounts of the asymmetric chain carbonate, dimethyl carbonate, and symmetric chain carbonate produced by the use of alcohols, respectively.

Example 1

A porous lithium aluminate support having a spinel structure (Li/Al=0.8/5, specific surface area: 95 m$^2$/g) was placed in an aqueous ammonia solution containing palladium chloride and cupric chloride so that 1 wt. % of palladium and 1.2 wt. % of copper were deposited on the support. The support is then dried at 110° C. and fired to 200° C. in an airy atmosphere, to obtain a solid catalyst on which palladium and copper were deposited. To a gaseous mixture of methyl nitrite and carbon monoxide charged into a gas passing reaction vessel having a fixed bed and the above solid catalyst was added ethanol. The resulting gaseous mixture was subjected to gaseous catalytic reaction, to give methyl ethyl carbonate. The reaction conditions are given below:

Gaseous starting mixture: methyl nitrite 15 vol. % and carbon monoxide 15 vol. %,
Methanol content/added ethanol (molar ratio)=0.8,
Hydrogen chloride: 60 ppm,
Amount of ethanol/methyl nitrite (molar ratio)=0.25,
Gas supply: supply rate (space velocity in terms of STP) 3,000 hr$^{-1}$, at 3 kg/cm$^2$G,
Reaction temperature under pressure: 120° C.,
Reaction period: 3 hours,
Amount of catalyst: 5 g (7 mL)
The results of the reaction are set forth in Table 1.

Example 2

The reaction procedures of Example 1 were repeated except that the amount of ethanol/methyl nitrite (molar ratio)

was changed to 0.5 (methanol content/added ethanol (molar ratio)=0.4). The results are set forth in Table 1.

Example 3

The reaction procedures of Example 2 were repeated except that the amount of ethanol/methyl nitrite (molar ratio) was changed to 1.0 (methanol content/added ethanol (molar ratio)=0.2). The results are set forth in Table 1.

Example 4

The reaction procedures of Example 2 were repeated except that ethanol was replaced with 2-propanol (isopropyl alcohol). The results are set forth in Table 1.

Example 5

The reaction procedures of Example 2 were repeated except that ethanol was replaced with 1-butanol. The results are set forth in Table 1.

Example 6

The reaction procedures of Example 2 were repeated except that the porous lithium aluminate was replaced with a zeolite support of NaY type (Si/Al=2.5 in terms of atomic ratio, specific surface area: 295 $m^2$/g). The results are set forth in Table 1.

Example 7

The reaction procedures of Example 2 were repeated except that the porous lithium aluminate was replaced with an active carbon support (specific surface area: 1,520 $m^2$/g). The results are set forth in Table 1.

Example 8

The reaction procedures of Example 2 were repeated except that the porous lithium aluminate was replaced with an alumina support (specific surface area: 145 $m^2$/g). The results are set forth in Table 1.

Reference Example 1

The reaction procedures of Example 2 were repeated except that ethanol was replaced with methanol in a molar ratio of 0.7 (total amount of methanol/methyl nitrite). The results are set forth in Table 1.

TABLE 1

| Example | Alcohol (Alc/MN) | Cat. Support | Produced Carbonate | Time (hr) | STY g/L · hr | Select. % |
|---|---|---|---|---|---|---|
| Ex. 1 | EtOH (0.25) | Lithium aluminate | MEC | 1 | 220 | 55 |
|  |  |  |  | 3 | 219 | 55 |
| Ex. 2 | EtOH (0.5) | Lithium aluminate | MEC | 1 | 348 | 59 |
|  |  |  |  | 3 | 346 | 59 |
| Ex. 3 | EtOH (1) | Lithium aluminate | MEC | 1 | 304 | 62 |
|  |  |  |  | 3 | 293 | 62 |
| Ex. 4 | 2-PrOH (0.5) | Lithium aluminate | MIPC | 1 | 337 | 55 |
|  |  |  |  | 3 | 333 | 54 |
| Ex. 5 | 1-BuOH (0.5) | Lithium aluminate | MBC | 1 | 320 | 53 |
|  |  |  |  | 3 | 290 | 51 |
| Ex. 6 | EtOH (0.5) | Zeolite (NaY type) | MEC | 1 | 215 | 59 |
|  |  |  |  | 3 | 213 | 58 |
| Ex. 7 | EtOH (0.5) | Active carbon | MEC | 1 | 293 | 58 |
|  |  |  |  | 3 | 292 | 58 |
| Ex. 8 | EtOH (0.5) | Alumina | MEC | 1 | 268 | 56 |
|  |  |  |  | 3 | 266 | 55 |
| Ref. 1 | MeOH (0.5) | Lithium aluminate | — | 1 | 0(612) | 0 |
|  |  |  |  | 3 | 0(611) | 0 |

Remarks:
EtOH: ethanol,
2-PrOH: 2-propanol,
1-BuOH: 1-butanol,
MeOH: methanol
Alc/MN: alcohol/methyl nitrate, molar ratio
Cat. support: catalyst support
Produced carbonate: produced asymmetric chain carbonate
Time: reaction period of time
STY: Y (space time yield of asymmetric chain carbonate)
Select.: selectivity (X) for asymmetric chain carbonate
Ref. 1: Dimethyl carbonate only is produced. The numeral in parentheses means STY of produced dimethyl carbonate.

What is claimed is:

1. A method for producing an asymmetric chain carbonate consisting of a step of reacting methyl nitrite, carbon monoxide and 0.25-1 moles of a lower alcohol per one mole of methyl nitrite, the lower alcohol being selected from the group consisting of ethanol, in a gaseous phase in the presence of a solid catalyst comprising palladium chloride and cupric chloride placed on a support, wherein the produced asymmetric carbonate is selected from the group consisting of methyl ethyl carbonate, wherein the palladium chloride and cupric chloride are deposited on the support in an amount of 0.1 to 10 wt. % per the amount of the compound.

2. The method of claim 1, wherein the support of the solid catalyst is a porous support.

3. The method of claim 2, wherein the porous support comprises a material selected from the group consisting of carbon, alumina, silica, silica alumina, zeo-lite, and lithium aluminate having a spinel structure.

4. The method of claim 1, wherein the reaction is performed under supply of hydrogen chloride in an amount of 0.01 to 1 mole per one mole of the platinum group metal in the catalyst.

* * * * *